(12) United States Patent
Wittig et al.

(10) Patent No.: US 8,361,050 B2
(45) Date of Patent: Jan. 29, 2013

(54) SPRING-LOADED CARTRIDGE CAP

(75) Inventors: Michael Wittig, West Chester, PA (US); John Barrella, Horsham, PA (US)

(73) Assignee: Animas Corporation, West Chester, PA (US)

( * ) Notice: Subject to any disclaimer, the term of this patent is extended or adjusted under 35 U.S.C. 154(b) by 572 days.

(21) Appl. No.: 12/569,953

(22) Filed: Sep. 30, 2009

(65) Prior Publication Data

US 2010/0082009 A1 Apr. 1, 2010

Related U.S. Application Data

(60) Provisional application No. 61/101,267, filed on Sep. 30, 2008.

(51) Int. Cl.
*A61B 19/00* (2006.01)
*A61M 37/00* (2006.01)
*A61M 5/315* (2006.01)

(52) U.S. Cl. .......... 604/403; 604/154; 604/218

(58) Field of Classification Search ............ 604/131, 604/134, 135, 140, 151–154, 218, 227, 500, 604/506, 507, 181–187; 128/DIG. 1, DIG. 12; 600/431, 432; 220/315, 319, 324–326
See application file for complete search history.

(56) References Cited

U.S. PATENT DOCUMENTS

| 7,666,169 B2* | 2/2010 | Cowan et al. ............ 604/228 |
| 2004/0116893 A1* | 6/2004 | Spohn et al. ............ 604/500 |

* cited by examiner

*Primary Examiner* — Philip R Wiest
(74) *Attorney, Agent, or Firm* — Wayne C. Jaeschke, Jr.

(57) ABSTRACT

Described is a spring-loaded cartridge cap for use in a drug infusion pump. The cap is ejected if it is not properly inserted into the pump. In one embodiment, the cap includes three detent pins that mate with detents in a cartridge chamber within the drug infusion pump. As the cap is inserted into the cartridge chamber of the drug infusion pump, the distal end of the cartridge compresses a coil spring within the cap. To secure the cap within the cartridge chamber, the cap is rotated such that each detent pin moves within a slot until a locking detent is engaged.

1 Claim, 5 Drawing Sheets

SPRING-LOADED CARTRIDGE CAP

FIELD OF THE INVENTION

The present invention relates, in general, to cartridge caps used in drug delivery devices and, more particularly, to spring-loaded and locking cartridge caps and methods for their use.

BACKGROUND OF THE INVENTION

The use of drug delivery devices for various types of drug therapy is becoming more common as the automated infusion of a drug may provide more reliable and more precise treatment to a patient.

Diabetes is a major health concern, as it can significantly impede on the freedom of action and lifestyle of persons afflicted with this disease. Typically, treatment of the more severe form of the condition, Type I (insulin-dependent) diabetes, requires one or more insulin injections per day, referred to as multiple daily injections. Insulin is required to control glucose or sugar in the blood, thereby preventing hyperglycemia which, if left uncorrected, can lead to ketosis. Additionally, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension, and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise. Thus, careful monitoring of blood glucose levels and the ability to accurately and conveniently infuse insulin into the body in a timely manner is a critical component in diabetes care and treatment.

In order to more effectively control diabetes in a manner that reduces the limitations imposed by this disease on the lifestyle of the affected person, various devices for facilitating blood glucose (BG) monitoring have been introduced. Typically, such devices, or meters, permit the patient to quickly, and with a minimal amount of physical discomfort, obtain a sample of their blood or interstitial fluid which is then analyzed by the meter. In most cases, the meter has a display screen which shows the BG reading for the patient. The patient may then dose themselves with the appropriate amount, or bolus, of insulin. For many diabetics, this results in having to receive multiple daily injections of insulin. In many cases, these injections are self-administered.

Due to the debilitating effects that abnormal BG levels can have on patients, i.e., hyperglycemia, persons experiencing certain symptoms of diabetes may not be in a situation where they can safely and accurately self-administer a bolus of insulin. Moreover, persons with active lifestyles find it extremely inconvenient and imposing to have to use multiple daily injections of insulin to control their blood sugar levels, as this may interfere or prohibit their ability to engage in certain activities. For others with diabetes, multiple daily injections may simply not be the most effective means for controlling their BG levels. Thus, to further improve both accuracy and convenience for the patient, insulin infusion pumps have been developed.

Insulin pumps are generally worn on the patient's body, either above or below their clothing. These relatively small, unobtrusive devices typically store a quantity of insulin in a replaceable cartridge and include a processing unit, a display screen, and input functions such as buttons or a keypad. Such pumps may include the ability to run multiple insulin delivery programs, such as basal and bolus programs, to eliminate the need for injections of insulin via needles and syringes, by providing medication via an infusion device that can be worn by the patient for an extended period of time, usually in the range of 1-3 days.

While the convenience of an insulin pump has helped to improve the lifestyle of diabetics and has lessened the impact of their disease on their normal activity, advances in insulin pumps are still needed. For example, in some diabetic patients who have dexterity problems, the patient cannot completely tighten the cartridge cap, resulting in potential loss of the pump air tight seal and loss of prime.

Therefore, it would be desirable for patients and caregivers to have a cartridge cap that locks into the cartridge chamber and that is ejected out of the chamber if it is not inserted properly.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF ILLUSTRATIVE EMBODIMENTS OF THE INVENTION

Figure 1A:
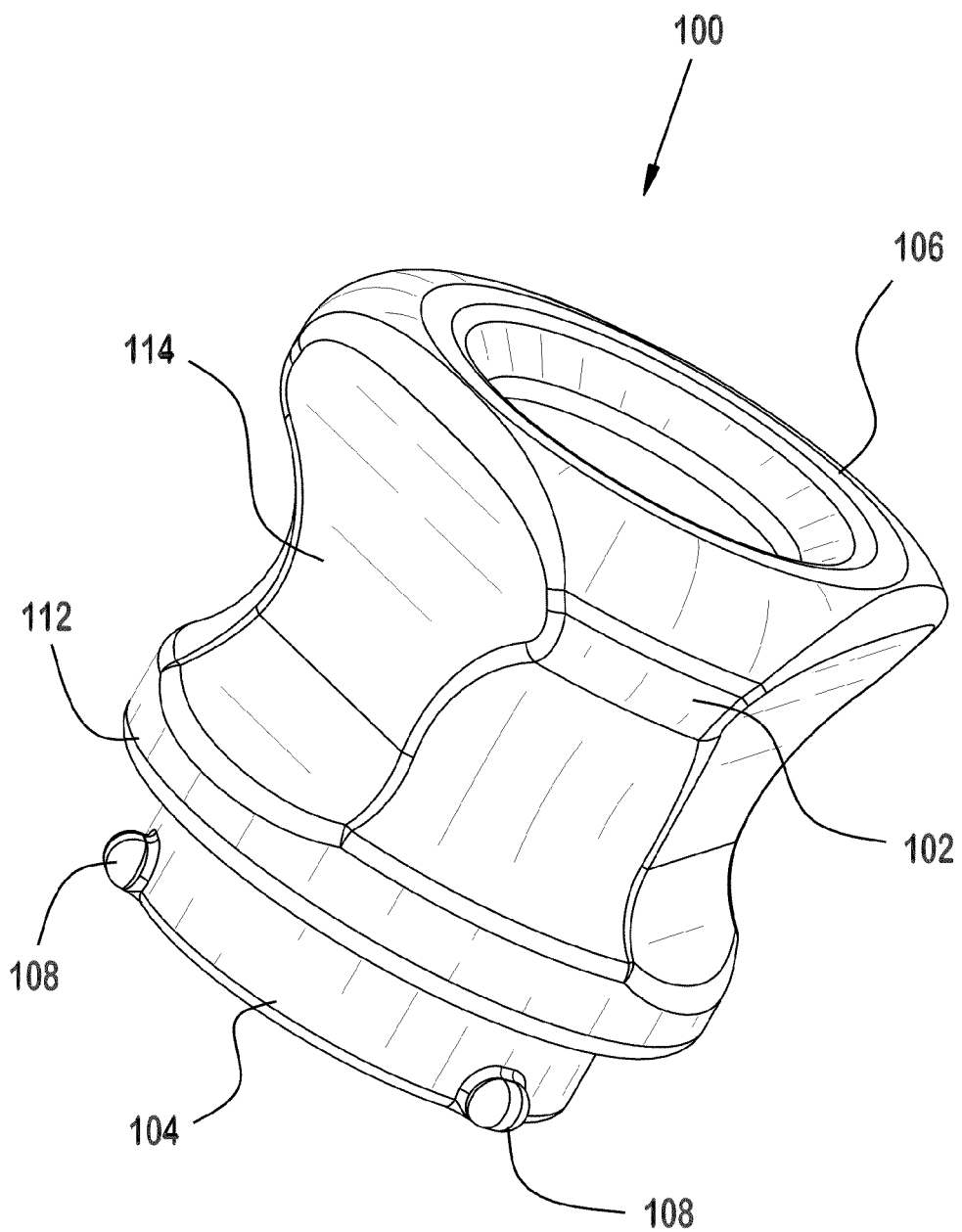
FIGS. 1A and 1B are perspective views of a cartridge cap according to an exemplary embodiment of the present invention.
Figure 1B:
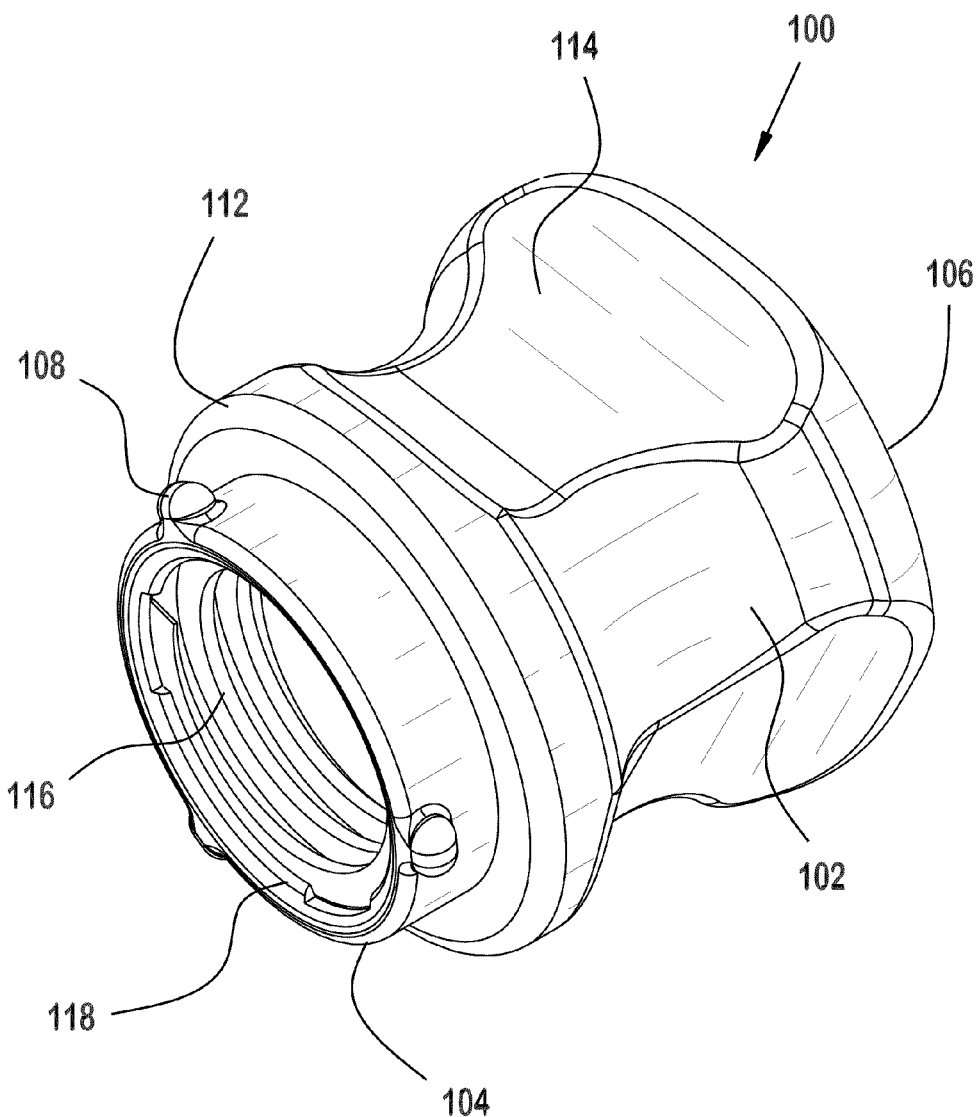
Figure 3:
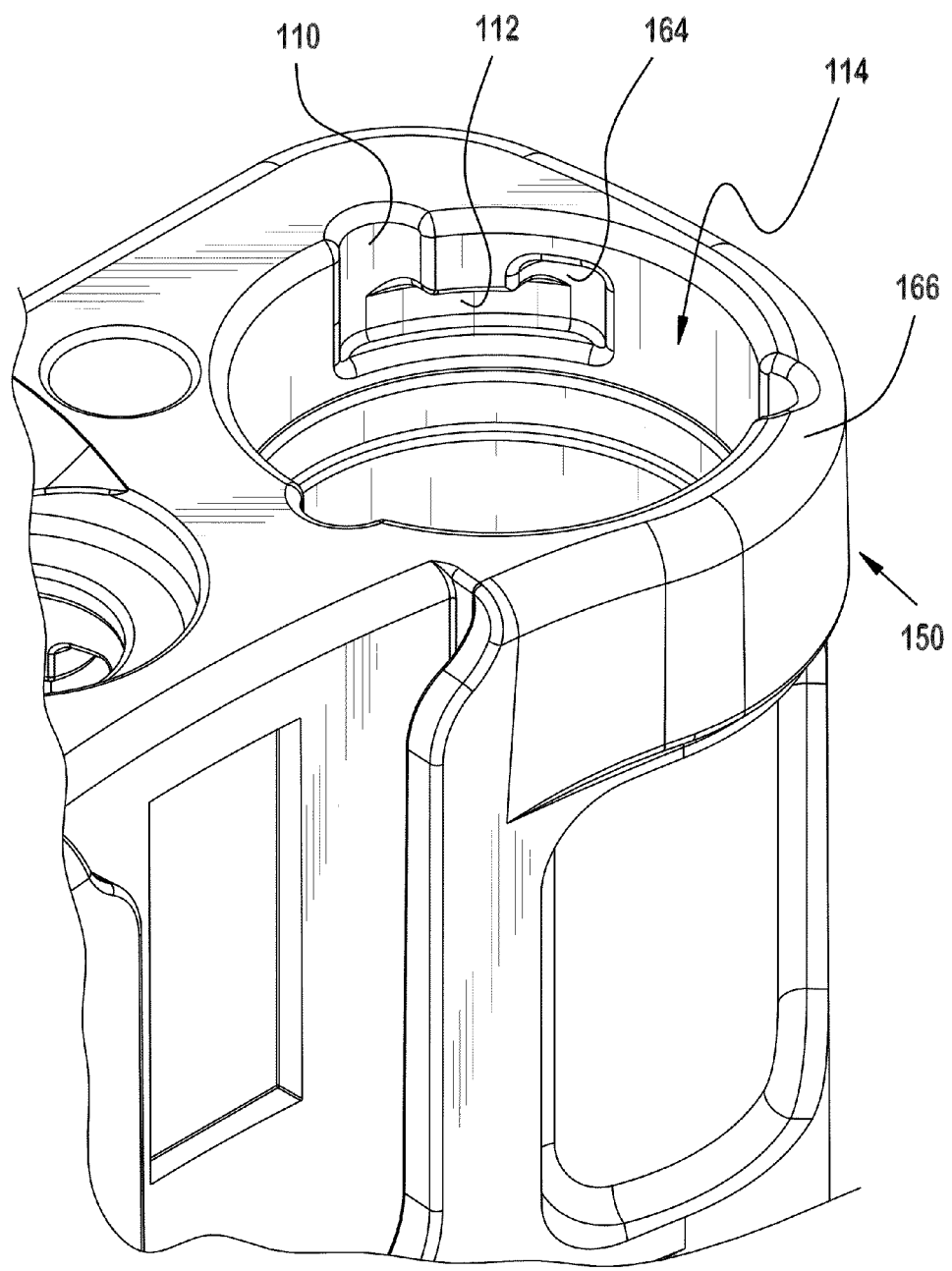
FIG. 3 is a perspective view of a portion of a drug infusion pump housing according to an exemplary embodiment of the present invention.

FIGS. 1A and 1B illustrate a cartridge cap 100 according to an exemplary embodiment of the present invention. The cartridge cap 100 is generally cylindrical in shape and includes a hollow body 102 with a first end 104 and a second end 106. The first end 104 includes at least one detent pin 108 that mates with at least one detent 110 and can move in at least one slot 112 (shown in FIG. 3) within a cartridge chamber 114 in a drug infusion pump 150. The body 102 includes an overmolded elastomeric polymer material layer 112 with contours that provide a gripping surface 114 for the user. Examples of elastomeric polymer materials that may be used in the present invention include thermoplastic urethane or a rubber material.

As shown in FIG. 1B, a coil spring 116 is located inside the first end 104 of the cap 100 and is held in the hollow space of the cap 100 by a lip 118 that is formed at least partially around the inner circumference at the first end 104 of the cap 100.

Figure 2:
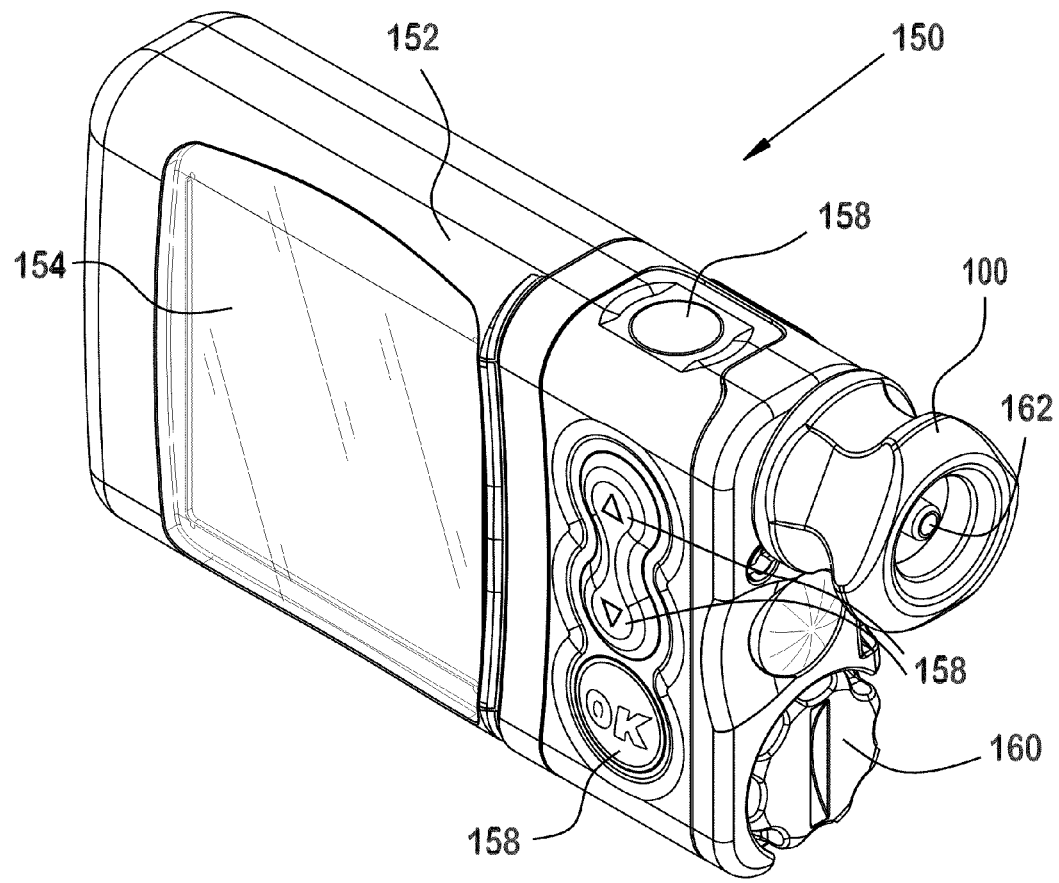
FIG. 2 is a perspective view of a drug infusion pump according to an exemplary embodiment of the present invention.

An exemplary embodiment of a drug infusion pump 150 that may incorporate a cartridge cap 100 of the present invention is illustrated in FIG. 2. The drug infusion pump 150 includes a housing 152, a display 154 for providing operational information to the user, a keypad with a plurality of navigational buttons 158 for the user to input information, a battery in a compartment (not shown) with a battery cap 160 for providing power to the drug infusion pump 150, processing electronics (not shown) and a drug delivery mechanism (e.g., an insulin pump and drive mechanism; not shown) for forcing a drug from a cartridge in a chamber through a side port 162 connected to an infusion set (not shown) and into the body of the user.

In one exemplary embodiment, there are three detent pins 108 on the first end 104 of the cap 100 separated by about 120 degrees (see FIG. 1B). In another exemplary embodiment, there are two detent pins 108 on the first end 104 of the cap 100 separated by about 180 degrees and in yet another exemplary embodiment there is one detent pin 108 on the first end 104 of the cap 100 (not shown). A thickening rib 166 may be included at the open end of cartridge chamber 114 to provide sufficient material strength for at least one detent 110 and at least one slot 112.

Figure 4:
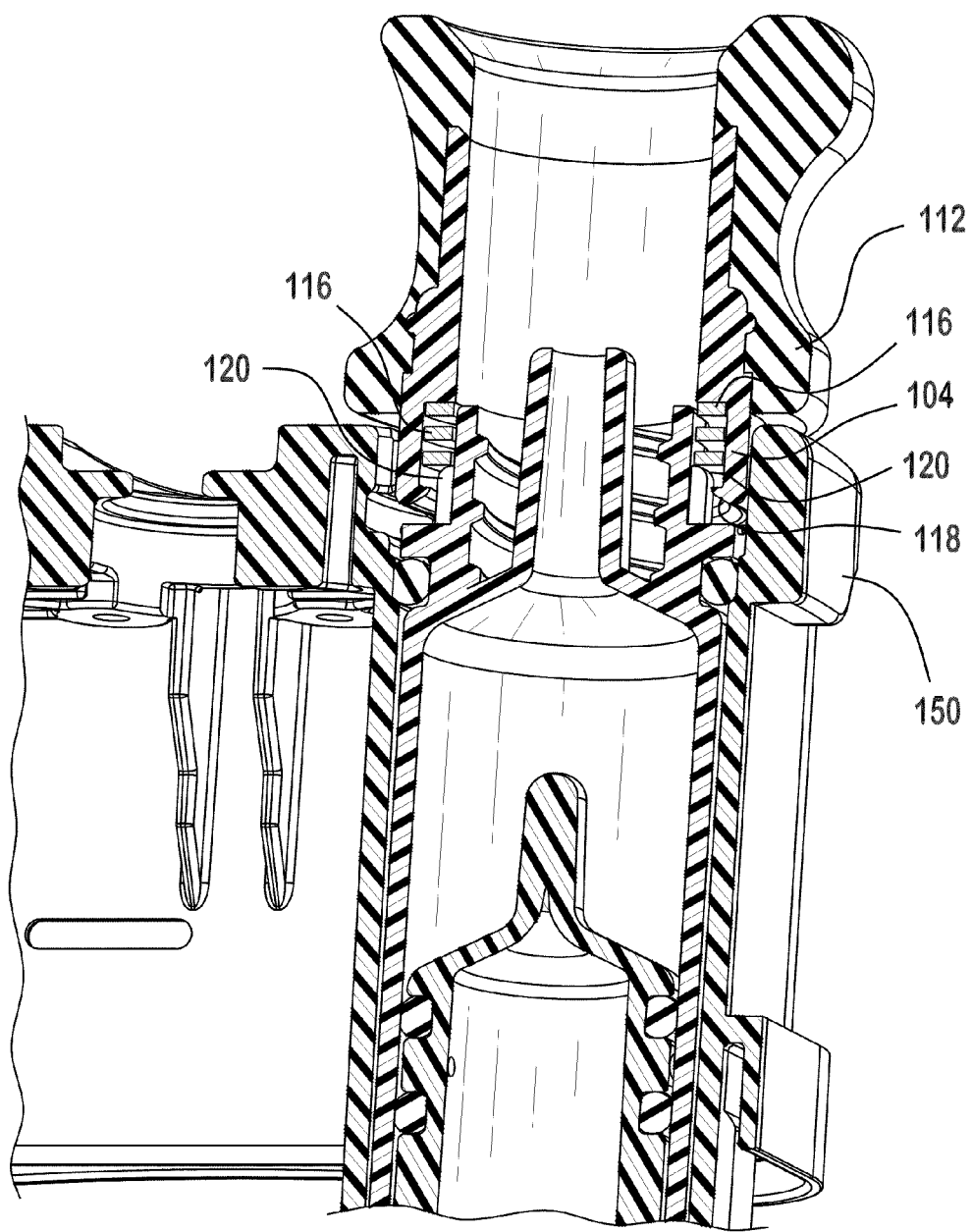
FIG. 4 is a cross-sectional view of a cartridge cap inserted into a drug infusion pump housing according to an exemplary embodiment of the present invention.

During use, the cap 100 is inserted into the cartridge chamber 114, pushed down onto the pump body and rotated clockwise until each pin 108 engages a locking detent 164 that locks the cap 100 within the chamber 114. As the cap 100 is inserted into the chamber 114 into which a cartridge has been inserted, the coil spring 116 engages a ledge 120 on a distal end of the cartridge such that the spring 116 is compressed (see FIG. 4). If the cap 100 is not inserted and rotated properly into the slots 112 inside the chamber 114, a spring force exerted on the cap 100 causes the cap 100 to be ejected from the chamber 114.

It will be recognized that equivalent structures may be substituted for the structures illustrated and described herein and that the described embodiment of the invention is not the only structure, which may be employed to implement the claimed invention. In addition, it should be understood that every structure described above has a function and such structure can be referred to as a means for performing that function. While embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A cartridge cap for a drug infusion device, comprising:
a cap having at least one detent pin,
at least one coil spring,
a lip around the inner circumference of the cap for retaining the at least one coil spring,
a drug infusion device for releasably receiving the cap, and
an opening in the drug infusion device having at least one slot for engaging the at least one detent pin and a ledge disposed circumferentially around the distal end of the opening in the drug infusion device and configured for the coil spring to bias against upon insertion of the cap into the opening in the drug infusion device,
wherein, the detent pin is configured to secure the cap in place at the opening in the drug infusion device by engaging the at least one slot and is also configured to eject the cap from the opening in the drug infusion device when the cap is situated on the opening in the drug infusion device without engaging the at least one detent pin with the at least one slot.

* * * * *